US007239926B2

(12) United States Patent
Goetz

(10) Patent No.: US 7,239,926 B2
(45) Date of Patent: Jul. 3, 2007

(54) SELECTION OF NEUROSTIMULATOR PARAMETER CONFIGURATIONS USING GENETIC ALGORITHMS

(75) Inventor: Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 556 days.

(21) Appl. No.: 10/767,692

(22) Filed: Jan. 29, 2004

(65) Prior Publication Data

US 2005/0060009 A1    Mar. 17, 2005

Related U.S. Application Data

(60) Provisional application No. 60/503,208, filed on Sep. 15, 2003.

(51) Int. Cl.
*A61N 1/00* (2006.01)
(52) U.S. Cl. .................................... 607/148; 607/46
(58) Field of Classification Search ............ 607/115, 607/148, 1–2, 46
See application file for complete search history.

(56) References Cited

U.S. PATENT DOCUMENTS

| 4,872,122 A | 10/1989 | Altschuler et al. |
| 4,895,574 A | 1/1990 | Rosenberg |
| 5,005,143 A | 4/1991 | Altschuler et al. |
| 5,240,009 A | 8/1993 | Williams |
| 5,280,792 A | 1/1994 | Leong et al. |
| 5,358,513 A | 10/1994 | Powell, III et al. |
| 5,383,910 A | 1/1995 | den Dulk |
| 5,443,486 A | 8/1995 | Hrdlicka et al. |
| 5,522,863 A | 6/1996 | Spano et al. |
| 5,626,140 A | 5/1997 | Feldman et al. |
| 5,645,069 A | 7/1997 | Lee |
| 5,673,367 A | 9/1997 | Buckley |
| 5,702,429 A | 12/1997 | King |
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |

(Continued)

FOREIGN PATENT DOCUMENTS

EP    0 653 224 A2    5/1995

(Continued)

OTHER PUBLICATIONS

Notification of Transmittal of the International Preliminary Examination Report dated Nov. 2, 2005, International Application No. PCT/US2004/030018, (9 pages).

*Primary Examiner*—Mark Bockelman
(74) *Attorney, Agent, or Firm*—Shunmaker & Sieffert, P.A.

(57) ABSTRACT

In general, the invention is directed to a technique for selection of parameter configurations for a neurostimulator using genetic algorithms. The technique may be employed by a programming device to allow a clinician to select parameter configurations, and then program an implantable neurostimulator to deliver therapy using the selected parameter configurations. In operation, the programming device executes an electrode configuration search algorithm to guide the clinician in the selection of electrode configurations. The search algorithm relies on a genetic algorithms to identify potential optimum electrode configurations within an electrode set. The genetic algorithms provide guidance in the electrode configuration selections process, interactively guiding the clinician by suggesting the configurations that are most likely to be efficacious given the results of tests already performed during an evaluation session.

51 Claims, 4 Drawing Sheets

U.S. PATENT DOCUMENTS

| | | |
|---|---|---|
| 5,782,885 A | 7/1998 | Andersson |
| 5,788,645 A | 8/1998 | Swanson et al. |
| 5,810,014 A | 9/1998 | Davis et al. |
| 5,867,386 A | 2/1999 | Hoffberg et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,995,868 A | 11/1999 | Dorfmeister et al. |
| 5,999,854 A | 12/1999 | Deno et al. |
| 6,052,624 A | 4/2000 | Mann |
| 6,081,750 A | 6/2000 | Hoffberg et al. |
| 6,129,745 A | 10/2000 | Sun et al. |
| 6,171,239 B1 | 1/2001 | Humphrey |
| 6,192,273 B1 | 2/2001 | Igel et al. |
| 6,263,230 B1 | 7/2001 | Haynor et al. |
| 6,269,267 B1 | 7/2001 | Bardy et al. |
| 6,308,102 B1 | 10/2001 | Sieracki et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,393,325 B1 | 5/2002 | Mann et al. |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,609,032 B1 | 8/2003 | Woods et al. |
| 6,658,287 B1 | 12/2003 | Litt et al. |
| 6,659,968 B1 | 12/2003 | McClure |
| 6,662,051 B1 | 12/2003 | Eraker et al. |
| 6,678,548 B1 | 1/2004 | Echauz et al. |
| 6,697,672 B2 | 2/2004 | Andersson |
| 6,704,595 B2 | 3/2004 | Bardy |
| 6,879,860 B2 * | 4/2005 | Wakefield et al. ............ 607/57 |
| 2001/0007950 A1 | 7/2001 | North et al. |
| 2002/0016699 A1 | 2/2002 | Hoggart et al. |
| 2002/0038294 A1 | 3/2002 | Matsugu |
| 2002/0045804 A1 | 4/2002 | Christopher et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0099303 A1 | 7/2002 | Bardy |
| 2002/0103512 A1 | 8/2002 | Echauz et al. |
| 2002/0106709 A1 | 8/2002 | Potts et al. |
| 2002/0123673 A1 | 9/2002 | Webb et al. |
| 2002/0133198 A1 | 9/2002 | Kramer et al. |
| 2002/0138013 A1 | 9/2002 | Guerrero et al. |
| 2002/0143262 A1 | 10/2002 | Bardy |
| 2002/0151992 A1 | 10/2002 | Hoffberg et al. |
| 2002/0169367 A1 | 11/2002 | Bardy |
| 2002/0169483 A1 | 11/2002 | Henry et al. |
| 2002/0173727 A1 | 11/2002 | Bardy |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0074032 A1 | 4/2003 | Gliner |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0130706 A1 | 7/2003 | Sheffield et al. |
| 2003/0158587 A1 | 8/2003 | Esteller et al. |
| 2003/0195569 A1 | 10/2003 | Swerdlow et al. |
| 2003/0216654 A1 | 11/2003 | Xu et al. |
| 2004/0019370 A1 | 1/2004 | Gliner et al. |
| 2004/0034394 A1 | 2/2004 | Woods et al. |
| 2004/0059395 A1 | 3/2004 | North et al. |
| 2004/0068199 A1 | 4/2004 | Echauz et al. |
| 2004/0073270 A1 | 4/2004 | Firlik et al. |
| 2004/0103001 A1 | 5/2004 | Mazar et al. |
| 2004/0129271 A1 | 7/2004 | Hickle |
| 2004/0158298 A1 | 8/2004 | Gliner et al. |

FOREIGN PATENT DOCUMENTS

| | | |
|---|---|---|
| EP | 0 653 224 B1 | 5/1995 |
| EP | 0 541 338 | 9/1996 |
| EP | 0 756 877 | 2/1997 |
| EP | 0 796 636 | 9/1997 |
| EP | 0 684 858 | 4/1998 |
| EP | 0 848 965 A2 | 6/1998 |
| EP | 0 882 469 | 12/1998 |
| EP | 1 192 971 | 4/2002 |
| EP | 0 848 965 B1 | 8/2003 |
| EP | 0 653 224 | 1/2004 |
| WO | WO 00/10455 | 3/2000 |
| WO | WO 01/17419 | 3/2001 |
| WO | WO 01/43823 | 6/2001 |
| WO | WO 01/56467 | 8/2001 |
| WO | WO 01/60445 | 8/2001 |
| WO | WO 01/82995 | 11/2001 |
| WO | WO 02/02622 | 1/2002 |
| WO | WO 02/15777 | 2/2002 |
| WO | WO 02/058536 | 8/2002 |
| WO | WO 03/026739 | 4/2003 |
| WO | WO 03/033070 | 4/2003 |
| WO | WO 03/037231 | 5/2003 |
| WO | WO 03/043690 | 5/2003 |
| WO | WO 03/094721 | 11/2003 |
| WO | WO 04/031919 | 4/2004 |

* cited by examiner

SELECTION OF NEUROSTIMULATOR PARAMETER CONFIGURATIONS USING GENETIC ALGORITHMS

This application claims the benefit of U.S. provisional application Ser. No. 60/503,208, filed Sep. 15, 2003, the entire content of which is incorporated herein by reference.

TECHNICAL FIELD

The invention relates to neurostimulation therapy and, more particularly, to techniques for selection of configurations for an implantable neurostimulator.

BACKGROUND

Implantable medical devices are used to deliver neurostimulation therapy to patients to treat a variety of symptoms or conditions such as chronic pain, tremor, Parkinson's disease, epilepsy, incontinence, sexual dysfunction, or gastroparesis. The implantable medical device delivers neurostimulation therapy via one or more leads that include electrodes located proximate to the spinal cord, pelvic nerves, sacrum, or stomach, or within the brain of a patient. In general, the implantable medical device delivers neurostimulation therapy in the form of electrical pulses.

A clinician selects values for a number of programmable parameters in order to define a parameter configuration for the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient, and duration for which the stimulation energy is delivered. In addition, the clinician also selects particular electrodes within an electrode set to be used to deliver the pulses, and the polarities of the selected electrodes. The electrode combinations and polarities may be referred to as an electrode configuration. Hence, a parameter configuration may involve a variety of parameters including electrode configuration, amplitude, pulse width, pulse rate, and duration.

The process of selecting parameter configurations can be time consuming, and may require a great deal of trial and error before an optimum electrode configuration is discovered. The optimum parameter configuration may be better than other configurations in balancing clinical results and side effects experienced by the patient. This balance represents overall efficacy of a parameter configuration. The process for selecting parameter configurations can be difficult due to the combinatorial possibilities of parameters, the complexity of the underlying biophysics, and subjective and possibly inconsistent feedback from the patient concerning observed efficacy for a given parameter configuration.

SUMMARY

In general, the invention is directed to a technique for selection of parameter configurations for a neurostimulator using genetic algorithms. The technique may be employed by a programming device to allow a clinician to select parameter configurations, and then program an implantable neurostimulator to deliver therapy using the selected parameter configurations.

A parameter configuration may define one or more parameters for delivery of neurostimulation, such as electrode configuration, amplitude, pulse width, pulse rate, or duration. For example, the parameter configurations may define electrode configurations that specify electrode combinations and polarities for an electrode set implanted in a patient. The electrode set may be carried by one or more implanted leads that are electrically coupled to the neurostimulator. In some embodiments, the parameter configurations may further define one or more parameters such as amplitudes, pulse widths, pulse rates, and durations of stimulation energy delivered by electrodes in the electrode configuration.

In operation, the programming device executes a parameter configuration search algorithm to guide the clinician in the selection of parameter configurations. The search algorithm relies on genetic algorithms to identify potential optimum parameter configurations, such as electrode configurations within an electrode set. The genetic algorithms provide guidance in the electrode configuration selections process, interactively guiding the clinician by suggesting the configurations that are most likely to be efficacious given the results of tests already performed during an evaluation session.

Genetic algorithms encode potential solutions to a problem as members of a population of solutions. This population is then judged based on a fitness function. The best performers, i.e., the most fit solutions, are then retained and a new generation is created based upon their characteristics. The new generation is composed of solutions similar in nature to the best performers of the previous generation.

This process of creation can use one or more techniques for generating new solutions. These techniques include cross-over, i.e., sharing of parts of a solution from one member to another, and mutation, i.e., random changes within a solution from one generation to the next. Hence, the genetic algorithm identifies solutions associated with the different parameter configurations, and updates the genetic algorithm by generating one or more successive generations of the solutions, e.g., by cross-over or mutation.

These techniques can be applied to the problem of parameter optimization, including selection of electrode configurations. Each potential solution, such as a parameter or electrode configuration, can be encoded as one member of the population. As an example, one solution might encode values for amplitude, rate, pulse width, and electrode combination of a stimulation device therapy. The fitness function used for selection then becomes the subjective efficacy rating assigned by the patient when the clinician tries the solution during a session. After some number of ratings are collected, the system 'kills' off the least fit, generates a new population based upon the more fit, and continues the cycle. This repeats until a satisfactory solution is discovered, or "evolved."

In one embodiment, the invention provides a method comprising selecting a first parameter configuration for a neurostimulator, receiving an indication of observed efficacy of the first parameter configuration, and selecting a second parameter configuration for the neurostimulator based on the indication of observed efficacy and a genetic algorithm.

In another embodiment, the invention provides a computer-readable medium comprising instructions to cause a processor to select a first parameter configuration for a neurostimulator, receive an indication of observed efficacy of the first parameter configuration, and select a second parameter configuration for the neurostimulator based on the indication of observed efficacy and a genetic algorithm.

In a further embodiment, the invention provides a device comprising a processor programmed to select a first parameter configuration for a neurostimulator, receive an indication of observed efficacy of the first parameter configuration, and select a second parameter configuration for the neurostimulator based on the indication of observed efficacy and a genetic algorithm.

The invention may provide a number of advantages. For example, the invention may allow a clinician to more quickly identify desirable parameter configurations such as electrode combinations, reducing the overall amount of time the clinician spends programming neurostimulation therapy for a patient. In contrast to random or idiosyncratic search techniques, a technique based on genetic algorithms is capable of learning from the evaluation of earlier parameter configurations, and developing a series of algorithms that lead to an optimum configuration. In general, the invention can reduce the length of a programming session for the clinician and the patient, and support selection of optimum electrode configurations to achieve overall efficacy. In addition, with the invention, it may be possible to identify optimal or near optimal parameter configurations that otherwise might not be identified by the clinician.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
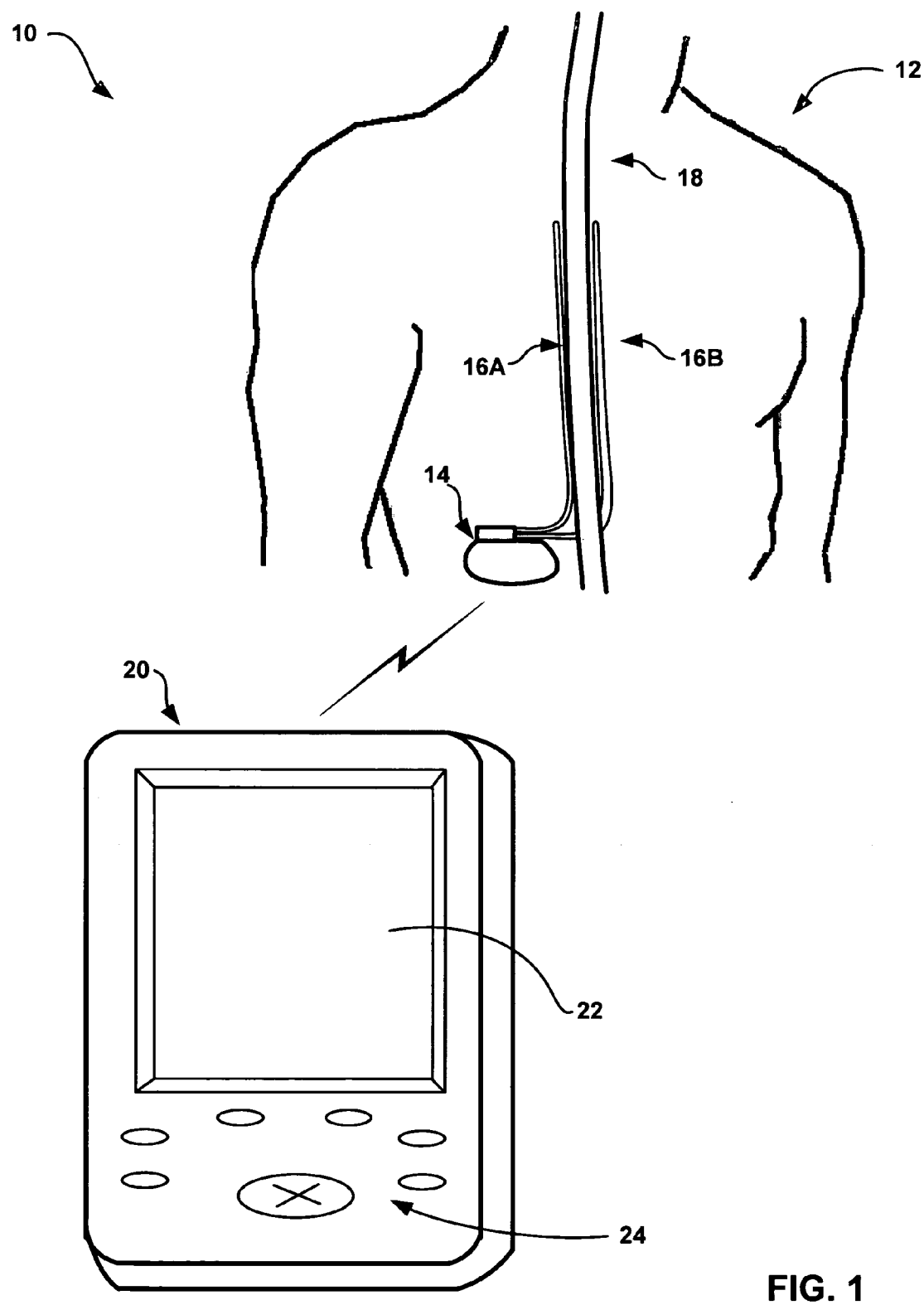
FIG. 1 is a diagram illustrating a system for programming and delivering neurostimulation therapy.

FIG. 1 is a diagram illustrating an example system 10 for programming neurostimulation therapy for and delivering neurostimulation therapy to a patient 12. System 10 includes an implantable medical device (IMD) 14 that delivers neurostimulation therapy to patient 12. IMD 14 may be an implantable pulse generator, and may deliver neurostimulation therapy to patient 12 in the form of electrical pulses. System 10 makes use of genetic algorithms for selection of parameter configurations.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown), sacrum (not shown) or stomach (not shown), and IMD 14 may deliver neurostimulation therapy to treat incontinence, sexual dysfunction, or gastroparesis.

IMD 14 delivers neurostimulation therapy to patient 12 according to one or more neurostimulation therapy programs. A neurostimulation therapy program may include values for a number of parameters, and the parameter values define a parameter configuration for delivery of the neurostimulation therapy delivered according to that program. In embodiments where IMD 14 delivers neurostimulation therapy in the form of electrical pulses, the parameters may include pulse voltage or current amplitudes, pulse widths, pulse rates, durations and the like. Further, each of leads 16 includes electrodes (not shown in FIG. 1), and the parameters for a program may include information identifying which electrodes have been selected for delivery of pulses according to the program, and the polarities of the selected electrodes. Hence, a parameter configuration may involve one or more of a variety of parameters including electrode configuration, amplitude, pulse width, pulse rate, and duration. Although the invention may be applicable to neurostimulation parameter configuration in general, including configuration of parameters such as amplitude, pulse width, pulse rate, duration and electrode configuration, the invention generally will be described for purposes of illustration in the context of determining an electrode configuration.

A selected subset of the electrodes located on leads 16 and the polarities of the electrodes of the subset collectively define an "electrode configuration." The electrodes may be arranged in a standard inline lead configuration, or as a surgical paddle lead, grid or other format. The electrodes may be associated with different target regions within a body of a patient. Electrode configurations refer to combinations of single or multiple cathode electrodes and single or multiple anode electrodes. Stimulation current flows between the cathodes and anodes for delivery of neurostimulation therapy. Hence, the polarities of the individual electrodes are another feature of the electrode configuration. Electrodes forming part of an electrode configuration may reside together on a single lead or on different leads System 10 also includes a programmer 20. Programmer 20 may, as shown in FIG. 1, be a handheld computing device. Programmer 20 includes a display 22, such as a LCD or LED display, to display information to a user. Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions.

A clinician (not shown) may use programmer 20 to program neurostimulation therapy for patient 12. In particular, the clinician may use programmer 20 to create neurostimulation therapy programs. As part of the program creation process, programmer 20 allows the clinician to identify parameter configurations that enable IMD 14 to deliver neurostimulation therapy that is desirable in terms of, for example, symptom relief, coverage area relative to symptom area, and side effects. Programmer 20 may also allow the clinician to identify parameter configurations that enable IMD 14 to deliver effective neurostimulation therapy with desirable device performance characteristics, e.g., low battery consumption. In addition, techniques as described herein may used to optimize therapy over the course of use of a chronically implanted IMD, e.g., by interaction between patient 12 and a patient programmer to record efficacy observations over time. In this case, a programmer carried by the patient may incorporate some or all of the functionality attributed to programmer 20 as described herein, including functionality designed to assist in identification of parameter configurations using genetic algorithms.

Programmer 20 controls IMD 14 to test parameter configurations in order to allow a clinician to identify desirable parameter configurations in an efficient manner. As will be described in greater detail below, in some embodiments, programmer 20 selects parameter configurations to test based on an electrode configuration search algorithm, as described herein. In particular, according to such an algorithm, programmer 20 may first control IMD 14 to test one or more electrodes to identify a first electrode configuration, and then test other electrode configurations based on guidance built into the search algorithm.

Other neurostimulation parameters such as amplitude, pulse width, pulse rate, and duration also may be evaluated with the electrode configuration. For example, various parameters may be observed simultaneously with observation of each electrode configuration. Alternatively, once a smaller set of electrode configurations has been identified as providing efficacy for a given baseline set of amplitude, pulse width and pulse rate, then different amplitude, pulse width and pulse rate parameters may be iteratively observed for that smaller set of electrode configurations. By controlling IMD 14 to test electrode configurations in an intelligent manner, programmer 20 allows the clinician to more quickly identify desirable electrode configurations. Duration of the delivery of neurostimulation energy also may be observed. In this manner, amplitude, pulse width, and pulse rate parameters need not be evaluated for every electrode configuration, and especially those electrode configurations that do not present a high probability of efficacy as inferred from the genetic algorithm solutions.

By controlling IMD 14 to test parameter configurations in an intelligent manner, programmer 20 allows the clinician to more quickly identify desirable parameter configurations, reducing the overall amount of time the clinician spends programming neurostimulation therapy for patient 12. For example, in contrast to existing neurostimulation programming systems that present electrode configurations in a random order or idiosyncratic search methodologies employed by clinicians, programmer 20 may select electrode configurations to test in a way that is more likely to enable desirable configurations to be selected earlier in the search. Consequently, the clinician may be able to end the search before all potential electrode combinations have been tested if one or more desirable configurations have already been identified, saving the amount clinician and patient time required to achieve an efficacious electrode configuration. In addition, with the invention, it may be possible to identify optimal or near optimal parameter configurations that otherwise might not be identified by the clinician.

Even if the clinician elects to test all potential electrode combinations, e.g., if the electrode set is small enough to make testing all electrode configurations practical, programmer 20 may reduce the time required to identify desirable electrode configurations by automating selection of each new configuration to test. Additionally, programmer 20 may improve the search process by collecting efficacy information for each combination tested. As will be described in greater detail below, programmer 20 may present a list of electrode configurations to the clinician, ordered according to the efficacy information, allowing the clinician to more easily identify and select desirable configurations. This list of electrode configurations may be ordered and updated according to newly observed efficacy information as additional electrode configurations are evaluated. Similar techniques may be applied for other neurostimulation parameters forming part of a parameter configuration, such as amplitude, pulse width, pulse rate, and duration.

In order to control IMD 14 to test electrode combinations, programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of parameter configurations associated with neurostimulation therapy programs. Neurostimulation therapy programs created by the clinician using programmer 20 may be transmitted to IMD 14 via telemetry, and/or may be transmitted to another programmer (not shown), e.g., a patient programmer, that is used by patient 12 to control the delivery of neurostimulation therapy by IMD 14.

Figure 2:
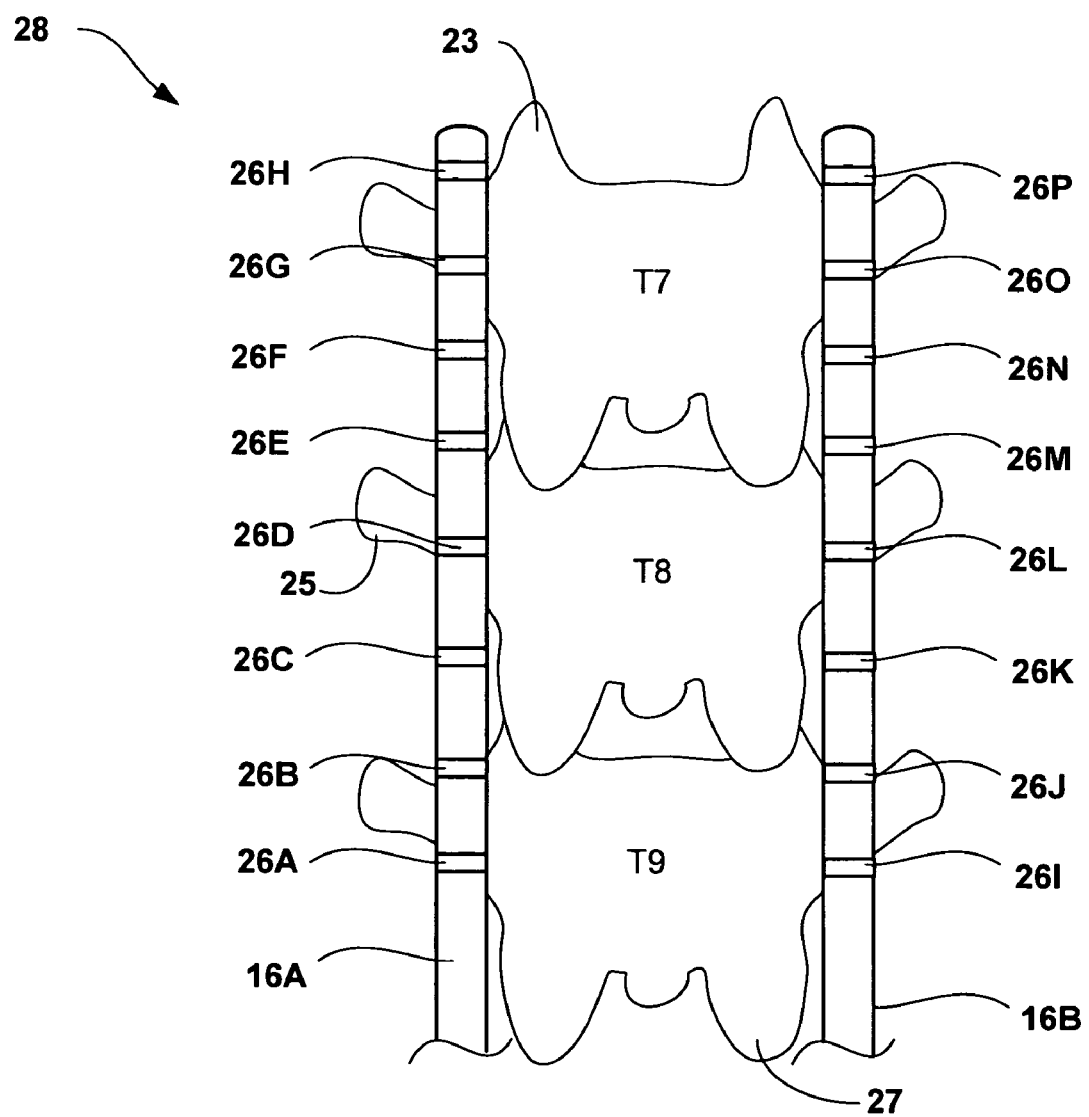
FIG. 2 is a diagram illustrating an example electrode set implanted proximate to the spine of a patient.

FIG. 2 is a block diagram illustrating an example configuration of leads 16. In the example configuration, lead 16A includes electrodes 26A–26H, and lead 16B includes electrodes 26I–26P. Hence, each lead 16 includes eight electrodes, although a lesser or greater number of electrodes are possible. Electrodes 26A–P (collectively "electrodes 26") may be ring electrodes. Electrodes 26 collectively form an electrode set 28 implanted within patient 12. As shown in FIG. 2, electrode set 28 includes eight electrodes on each of the two leads 16, which, as shown in FIG. 1, are implanted such that they are substantially parallel to each other and spinal cord 18 (FIG. 1), on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 28 may be described as a two-by-eight, side-by-side, upwardly oriented configuration. Of course, electrode set 28 is provided for purposes of example, and the invention may be applicable to other types of leads and electrode sets, including single lead electrode sets, flat paddle leads, grid arrays, and the like.

Such an electrode set is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20. In the example of FIG. 2, electrodes 26 are placed on opposite sides of the T7 vertebra 23, T8 vertebra 25 and T9 vertebra 27 of a human spine.

IMD 14 (FIG. 1) may deliver neurostimulation via any combination of electrodes 26. IMD 14 may independently activate each electrode 26 of set 28 to act as a cathode or anode for a configuration, and .each configuration will include at least one cathode and at least one anode. In some embodiments, it is possible that an electrode configuration may include a single electrode 26 acting as the cathode, with a can of IMD 14, i.e., the IMD housing, acting as the anode for the configuration.

In an electrode configuration, electrons flow from one or more electrodes acting as anodes for the configuration to one or more electrodes acting as cathodes for the configuration. The current between anodes and cathodes stimulates neurons between and proximate to the anodes and cathodes. Generally speaking, an electrode configuration enables desirable neurostimulation therapy when current is delivered in a direction and with an intensity sufficient to stimulate specific neurons or a sufficient number of specific neurons to alleviate a symptom without causing unacceptable side effects. Further, an electrode configuration enables desirable neurostimulation therapy when the symptom is alleviated without resorting to undesirably high pulse amplitudes.

As mentioned above, programmer 20 selects individual electrodes 26 or electrode configuration to test to allow a clinician to identify desirable electrode configuration according to an electrode search algorithm. Programmer 20 may select an appropriate search algorithm based on the configuration of electrode set 28, and may select electrodes 26 or electrode configurations based on the selected search algorithm. Programmer 20 controls IMD 14 to test a selected electrode 26 or electrode combination by controlling IMD 14 to deliver neurostimulation via the selected electrode 26 or combination.

In some embodiments, programmer 20 may first control IMD 14 to test one or more of electrodes 26 individually to identify the individual electrode or electrodes 26 which will act as a first cathode. In other embodiments, programmer 20 starts with a combination of selected electrodes 26. Generally, a clinician implants leads 16 in a location such that the center of electrode set 28 is proximate to an area that the clinician believes should be stimulated in order to alleviate symptoms. Therefore, programmer 20 may test electrodes 26 as the first cathode in an order such that electrodes 26 located centrally within electrode set 28, e.g., electrodes 26D–E and 26L–M illustrated in FIG. 2, are tested before peripherally located electrodes. If the clinician's estimation of the target region is inaccurate, programmer 20 will continue to test individual electrodes 26 in such an order until one of the electrodes 26 that enables desirable neurostimulation therapy when activated as the first cathode is identified. Initially locating a first cathode provides a "coarse" optimization of electrode combinations, allowing programmer 20 and the clinician to quickly identify the general area to which neurostimulation therapy should be delivered.

Programmer 20 may then control IMD 14 to test electrode configurations that include the first cathode. The various electrode configurations may be tested with a common set of stimulation parameters, such as a common voltage or current amplitude, frequency, and pulse width. In some embodiments, a series of different stimulation parameters may be applied for each combination of electrodes to test not only the efficacy of electrode combinations, but also electrode combinations with particular stimulation parameters such as amplitude, frequency and pulse width. Hence, an electrode configuration may apply to the combination of electrodes forming part of the neurostimulation parameter configuration, and the parameters associated with delivery of neurostimulation energy via the electrodes, such as amplitude, pulse width and pulse rate, may form another part of the parameter configuration.

Programmer 20 may control IMD 14 to try different ones of electrodes 26 as the first anode in a pair with the first cathode, and may add additional anodes and/or cathodes. In accordance with an embodiment of the invention, programmer 20 controls IMD 14 to test remaining electrodes 26 as first anodes, and additional anodes or cathodes, based on electrode configurations identified by genetic algorithms. The genetic algorithms may be employed by programmer 20 to allow a clinician to select electrode configurations, and then program IMD 14 to lead to optimum electrode configurations.

The search algorithm uses the genetic algorithms to select possible electrode configurations based on the efficacies of parameter configurations already observed in the course of evaluation. The previous observations are used to refine the algorithms. In particular, the observations are used to compare the genetic algorithms to an applicable fitness function, and then refine, or "evolve," the structure of the algorithms to select optimum parameter configurations, such as electrode configurations. The first generation of the genetic algorithms may be established based on an existing set of data, or developed based on the input of a neurostimulation expert, and then updated to produce new algorithms based on efficacy information for newly considered parameter configurations. With the aid of genetic algorithms, a programmer 20 provides a clinician with suggestions of electrode configurations that are likely to be efficacious given observations already obtained during the selection process. In response, the clinician may select the suggested electrode configurations next. In some cases, the selection of electrode configurations, or other parameters, may be automated in response to suggestions generated using the genetic algorithms. In other cases, the selection of the parameter configurations may require human intervention from the clinician, but be aided by the suggestions.

Figure 3:
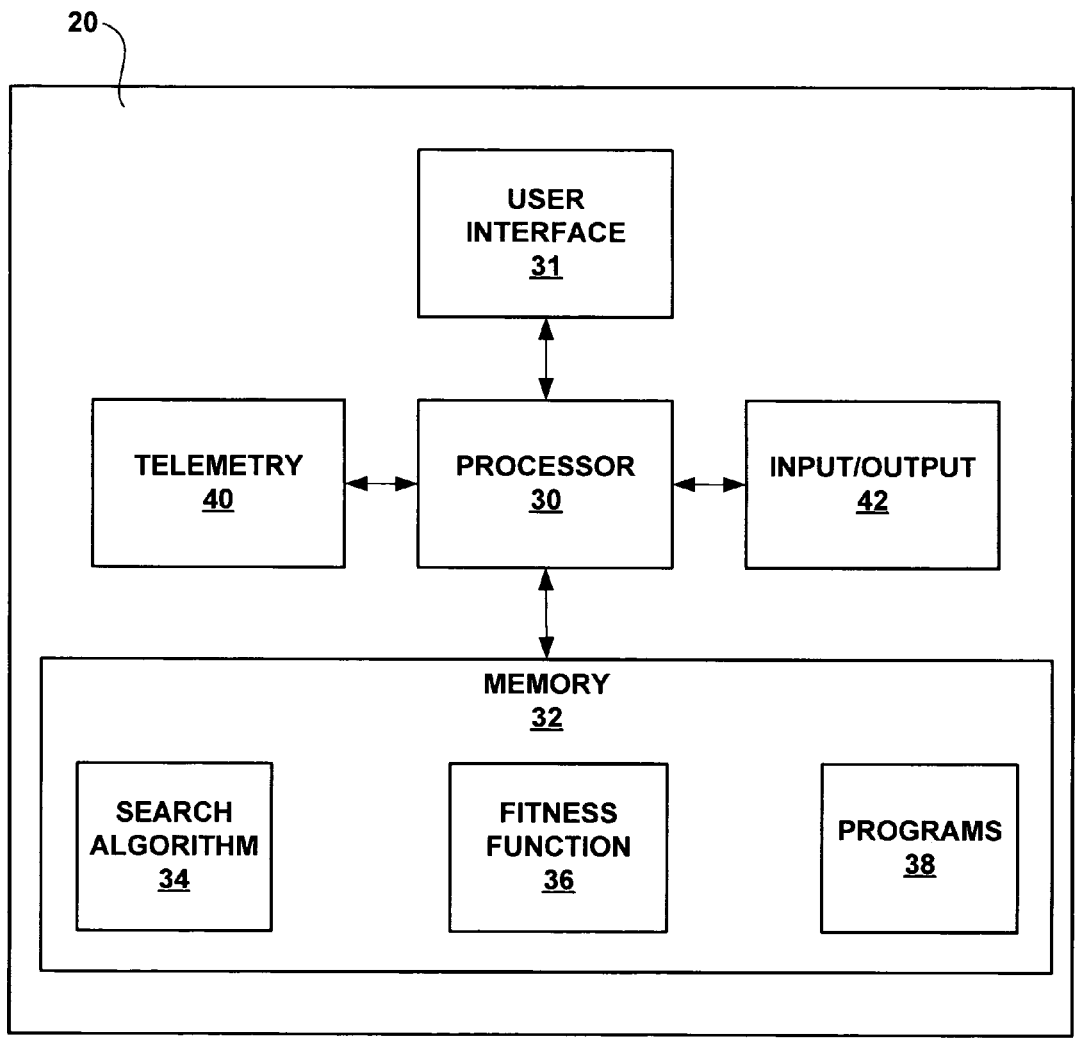
FIG. 3 is a block diagram illustrating a programming device used to identify desirable parameter configurations for neurostimulation therapy programs.

FIG. 3 is a block diagram illustrating an example configuration of programmer 20. A clinician or other user may interact with a processor 30 via a user interface 31 in order to identify and select electrode configurations as described herein. User interface 31 may include display 22 and keypad 24 (FIG. 1), and may also include a touch screen or peripheral pointing devices as described above. Processor 30 may also provide a graphical user interface (GUI) via user interface 31 to facilitate interaction with a clinician, technician, or other medical personnel. Processor 30 may include a microprocessor, a controller, a DSP, an ASIC, an FPGA, discrete logic circuitry, or the like.

Clinician programmer 20 also includes a memory 32. Memory 32 may include program instructions that, when executed by processor 30, cause clinician programmer 20 to perform the functions ascribed to clinician programmer 20 herein. For example, processor may execute one or more parameter configuration search algorithms 34 stored within memory 32. In particular, processor 30 may execute an electrode configuration search algorithm to select individual electrodes 26 or electrode combinations to test to allow the clinician to identify desirable electrode combinations. Search algorithm 34 executes based on the genetic algorithm, which yields electrode configurations within electrode set 28 with increased efficacy. In particular, search algorithm 34 is evaluated according to one or more fitness functions 36 stored within memory 32 to generate new algorithms designed to lead to better parameter configurations.

Hence, programmer 20 provides interactive guidance to a clinician during the process of optimizing implantable device parameters. In particular, programmer 20 guides the clinician by suggesting the electrode configurations that are most likely to be efficacious given the results of tests already performed during the source of an evaluation session. This is accomplished by building the genetic algorithm based on previous results.

Search algorithm 34, in the form of genetic algorithms that evolve according to search results, encode potential solutions to a problem as members of a population of solutions. This population is then judged based on fitness function 36. The best performers, i.e., the most fit solutions, are then retained and a new generation is created based upon their characteristics. The new generation comprises solutions similar in nature to the best performers of the previous generation. This process of creation can use one or more techniques for generating new solutions. These techniques include cross-over, i.e., sharing of parts of a solution from one member to another, and mutation, i.e., random changes within a solution from one generation to the next.

Each potential solution (parameter configuration) can be encoded as one member of the population. As an example, one solution might encode values for amplitude, rate, pulse width, and electrode combination of a stimulation device therapy. The fitness function used for selection then becomes the efficacy rating assigned by the patient when the clinician tries the parameter configuration corresponding to the solution during a session. In general, efficacy refers to the balance between therapeutic benefit and undesirable side effects. As examples, efficacy can be observed by verbal feedback from the patient concerning therapeutic benefit and side effects, marking of a pain/parasthesia map, objective measurement using pain rating scales, quantification of side effects, a combination of the forgoing, or other observation techniques. After some number of ratings are collected, the system 'kills' off the least fit solution, generates a new population based upon the more fit, and continues the cycle. This repeats until a satisfactory solution is discovered, or "evolved."

As an illustration, genetic algorithms can be applied to the problem of determining the best electrode configuration for a specific individual. The solutions to this problem are possible configurations of the electrodes on the leads, such as the electrodes 26 depicted in FIG. 2. These solutions might be encoded by a series of characters—'o' representing off, '+' representing the anode, and '−' representing the cathode. A lead configuration for a 2×8 system as shown in FIG. 2 may then be encoded as follows.

| Lead 1 | Lead 2 |
|---|---|
| oooo+−oo | oo−+oooo |

Hence, in the above example, a fifth electrode (+) in the first lead and a fourth electrode (+) in the second lead represent selection as anodes, whereas the sixth electrode (−) in the first lead and the third electrode (−) in the second lead represent selection as cathodes. A population of such solutions could then be generated at random to seed genetic search algorithm 34.

Alternatively, the search algorithm 34 can be seeded with a population hand-picked by system designers as a good starting point. For this example, a population size of three will be chosen. In practice, this population size may be larger. The set of three genetic algorithm solutions may be represented as follows:

| | Lead 1 | Lead 2 |
|---|---|---|
| Solution #1 | oooo+−oo | oo−+oooo |
| Solution #2 | +−oooooo | oooooo+− |
| Solution #3 | ooo+−ooo | oooo+−oo |

The above solutions can then each be trialed by the clinician and rated by the patient in terms of efficacy, which may reflect both positives such as therapeutic benefit and negatives such as side-effects. Assume, for the purposes of this example, that the first and last solutions (#1 and #3) were rated highly and the middle solution (#2) was rated poorly. Processor 30 in programmer 20 would then generate a new set of solutions using crossover and/or mutation. In this domain, examples of crossover may involve swapping selected single electrodes from one solution to another, swapping bipoles from one solution to another, and swapping ranges of electrodes, e.g., the bottom four, middle four, or top four electrode values with another solution. Examples of mutation may involve adding a single electrode at a random location (cathode or anode), adding a single electrode near exising electrodes (cathode or anode), adding a pair of electrodes, removing a single electrode, inveting polarities of pairs (cathode to anode, anode to cathode), inverting polarities of single electrodes, shifting all electrodes up or down a lead, and randomly turning two adjacent off-electrodes into a bipole pair. Other variations on crossover or mutation may be viable.

All of these crossover and mutation techniques need not be used at one. In general, one may try to balance speed of convergence with optimality of the end result. For instance, since is is known that the problem is relatively dependent on the locations of the electrodes, experimenting "near" a known good electrode combination will cause solutions to converge more quickly. For example, mutation may be conducted only near existing electrodes. However, this approach may cause the algorithm to exclude more radical solutions that may work better. In this case, mutation on a more random basis may be more desirable. The solution population for the next generation might look as follows:

| | Lead 1 | Lead 2 | |
|---|---|---|---|
| Solution #4 | ooo+−ooo | oo−++−oo | //new solution formed by crossing over first 4 electrodes of second lead of old solution #1 to old solution #3 |
| Solution #5 | o+−o+−oo | oo−+oooo | //new solution formed by mutating 2nd and 3rd electrodes of old solution #1 |
| Solution #6 | ooo+−ooo | oooo+−oo | //new solution formed by bringing forward old solution #3 unchanged. |

This process of creating new generations of solutions, e.g., by cross-over, mutation, or a combination of both, then repeats until a satisfactory solution is reached. For example, the process may repeat until one of the solutions satisfies an efficacy threshold. This process may be implemented, as described herein, as a feature of clinician programmer 20, with the evolution of solutions occurring within a clinical visit.

As an alternative, or in addition, this process may also be implemented within a patient programmer. In this configuration, the patient would initiate a new cycle when he or she was dissatisfied with the current therapy. The patient device would then present the new population and capture the patient's efficacy ratings. The patient could then repeat this process at his or her leisure until an optimal solution was achieved.

Processor 30 collects information relating to the parameter configurations identified by the genetic algorithm process, and stores the information in memory 32 for later retrieval and review by the clinician to facilitate identification of desirable parameter configurations. Neurostimulation therapy programs 38 created by the clinician may be stored in memory 32, and information identifying electrode configurations selected by the clinician to be utilized for one or more of programs 38 with the aid of the genetic algorithms may be stored as part of the programs 38 within memory 32.

Memory 32 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 30 controls IMD 14 to test selected individual electrodes 26 or electrode combinations, by controlling IMD 14 to deliver neurostimulation therapy to patient 12 via the selected individual electrodes 26 or electrode combinations via a telemetry circuit 40. Processor 30 may transmit programs 38 created by the clinician to IMD 14 via telemetry circuit 40, or to another programmer used by the patient to control delivery of neurostimulation therapy via input/output circuitry 42. I/O circuitry 42 may include transceivers for wireless communication, appropriate ports for wired communication or communication via removable electrical media, or appropriate drives for communication via removable magnetic or optical media.

Using the genetic algorithm process, programmer 20 provides suggestions on which electrode configurations are most likely to be efficacious. In this manner, the genetic algorithms can be used to guide the clinician to a set of optimum parameter configurations, such as electrode configurations, for evaluation, reducing the number of observations that need be made to ensure a good outcome. In other words, the genetic algorithms may permit the clinician to avoid a number of parameter configurations that, based on previous experience, are unlikely to yield efficacious results. Rather, the genetic algorithms lead to solutions that provide optimum electrode configurations. The genetic technique benefits from past observations, and is more likely to produce optimum efficacy results.

Figure 4:
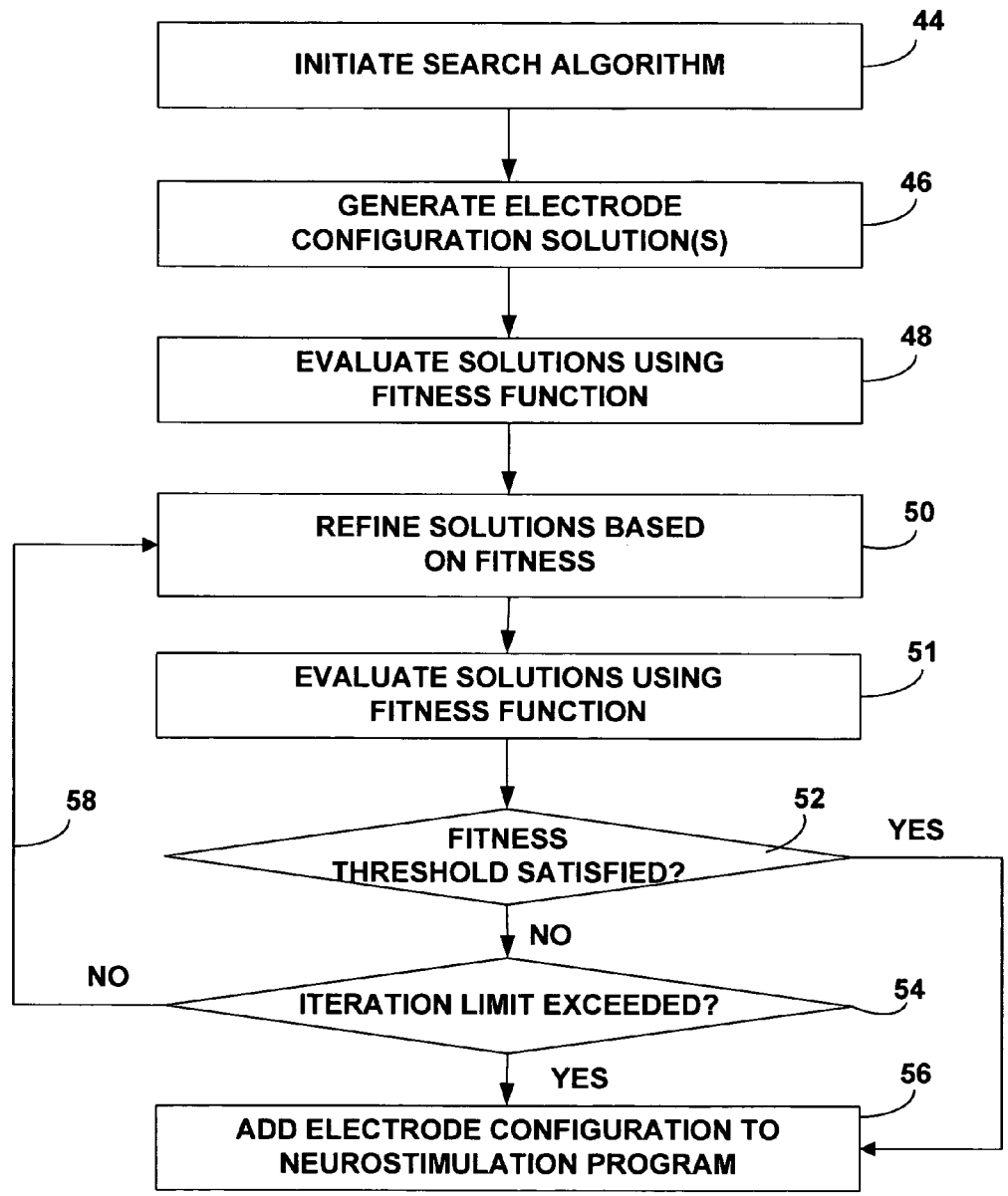
FIG. 4 is a flow diagram illustrating application of genetic algorithms to select electrode configurations.

FIG. 4 is a flow diagram illustrating a process that is executable by a programmer to select parameter configurations using genetic algorithms as described herein. The example of FIG. 4 is directed to electrode configurations for purposes of illustration. As shown in FIG. 4, the process involves initiating a genetic search algorithm (44) to generate one or more electrode configuration solutions (46). The solutions are evaluated using a fitness function (48). The fitness function may be based on overall efficacy ratings provided by a patient. The efficacy rating can be solicited from the patient by the clinician, or entered directly by the patient. Again, efficacy refers to the balance between therapeutic benefit and undesirable side effects. As examples, efficacy ratings can be obtained by verbal feedback from the patient concerning therapeutic benefit and side effects, marking of a pain/parasthesia map, objective measurement using pain rating scales, quantification of side effects, a combination of the forgoing, or other observation techniques.

Then, the process involves genetically refining the solutions based on fitness (50). For example, the solutions may be genetically refined using techniques such as cross-over, i.e., by sharing of parts of a solution from one member to another, and/or mutation, i.e., by incorporating random changes within a solution from one generation to the next, or combinations of both. Upon evaluating the solutions with the fitness function (51), the fitness level is compared to a fitness threshold (52). The fitness threshold may relate to a desired efficacy threshold. Again, the efficacy may be rated positively in terms of pain relief or other therapeutic benefit, and negatively in terms of side effects of the therapy. The search capability can be implemented as a feature in an implantable device programmer 20.

When a fitness threshold is satisfied (52), the electrode configuration or configurations represented by the present solution or set of solutions are added to a neurostimulation program for selection by the clinician (56). If the fitness threshold is not satisfied (52), and an iteration limit has been exceeded (54), the algorithm terminates. In this case, the current electrode configuration may be selected and added to a neurostimulation program (56), or the clinician may be prompted to take other action. If the iteration limit is not exceeded (54), the genetic algorithm process continues iteratively (58) until the efficacy threshold is satisfied or the iteration limit is exceeded. The iteration limit may be established by the clinician.

If the clinician stops the search before all possible combinations of electrodes 26 have been tested, programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, programmer 20 may allow clinician to spend less time searching for desirable electrode combinations in a subsequent programming session. Specifically, the programs created using the bracket combinations may enable desirable neurostimulation therapy similar to that provided in a program created with the most recently tested combination, and may be provided to patient 12 so that patient 12 can experiment with the bracket programs outside of the clinic.

As described herein, programmer 20 controls IMD 14 to test electrode configurations by controlling IMD 14 to deliver neurostimulation therapy via combinations of electrodes. In addition, programmer 20 may be configured to facilitate a search for other optimum therapy parameters. For example, the clinician or programmer 20 may select desired starting points for pulse amplitude, rate and pulse width for each electrode configuration, and programmer 20 may ramp the amplitude from the starting point at a first rate of amplitude increase using similar techniques. Programmer 20 may increase the amplitude in, for example, a linear or step-wise fashion. In some embodiments, the clinician or patient 12 may control the rate of amplitude increase. The clinician or patient 12 stops the ramping of the amplitude when the stimulation causes discomfort, or other undesirable side effects.

Programmer 20 may reduce the amplitude at the time the ramp is stopped by some amount, e.g., a percentage, and ramps the amplitude again in order to allow the clinician and/or patient 12 to identify the amplitude that provides the best neurostimulation therapy. This second time, programmer 20 may ramp the amplitude at a slower rate of amplitude increase in order to facilitate identification of the point where best neurostimulation is achieved. Again, in some embodiments, the clinician or patient 12 may control the amplitude.

Programmer 20 stores the amplitude at the time when the best neurostimulation therapy is indicated by the clinician and/or patient 12, and rating information for the electrode combination. The clinician and/or patient 12 may provide efficacy rating information, e.g., a numerical value for one or more metrics for rating the combination, which relates to the efficacy enabled by the combination or the side effects resulting from use of the combination, or both.

The clinician may use rating information and/or the amplitude values stored for each tested combination to identify desirable electrode configurations. The configurations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Various embodiments of the invention have been described. However, one skilled in the art will appreciate that various additions and modifications can be made to these embodiments without departing from the scope of the invention. The invention may be generally applicable to any programming optimization problem in which the feedback from a configuration is available relatively quickly and within the context of the clinical programming environment. This includes the stimulation therapies for pain and movement disorders and may include other stimulation-based therapies as well.

For example, although programmer 20 has been described herein as a hand-held computing device, programmer 20 may take the form of any type of computing device, such as a laptop or desktop computer, may access resources, such as memory 54, via a computer network, such as a LAN, WAN, or the World Wide Web. Further, programmer 20 may include a plurality of computing devices, which may communicate to provide the functionality ascribed to programmer 20 herein via a computer network.

Although described herein as associated with and interacting with a clinician, i.e., a clinician programmer, programmer 20 may be associated with patient 12, i.e., a patient programmer. In some embodiments, patient 12 may simply interact with programmer 20 in place of the clinician for some or all of the electrode combination identification process. In other embodiments, patient 12 may perform parts of the configuration identification process without being supervised by the clinician, e.g., away from the clinic, using a patient programmer. These and other embodiments are within the scope of the following claims.

The invention claimed is:

1. A method comprising:
selecting a first electrode configuration for a neurostimulator;
receiving an indication of observed efficacy of the first electrode configuration; and
selecting a second electrode configuration for the neurostimulator based on the indication of observed efficacy and a genetic algorithm, wherein each of the electrode configurations defines a combination of particular electrodes selected from a set of electrodes for delivery of neurostimulation energy, the electrode configurations further defining polarities for each of the electrodes in the combination.

2. The method of claim 1, wherein the electrodes are carried by two or more implanted leads.

3. The method of claim 2, wherein the electrodes are associated with different target regions within a body of a patient.

4. The method of claim 2, wherein the leads are implanted proximate a spine of a patient.

5. The method of claim 1, further comprising iteratively selecting additional electrode configurations for the neurostimulator based on observed efficacy of preceding electrode configurations and the genetic algorithm.

6. The method of claim 5, further comprising terminating the iterative selection of the additional electrode configurations when one or more termination criteria are satisfied.

7. The method of claim 6, wherein the termination criteria include selection of one of the electrode configurations with an observed efficacy that satisfies a threshold efficacy.

8. The method of claim 1, further comprising:
iteratively selecting additional electrode configurations for the neurostimulator based on observed efficacy of preceding electrode configurations and the genetic algorithm;
terminating the iterative selection of the additional electrode configurations at a final electrode configuration when one or more termination criteria are satisfied; and
programming the neurostimulator to employ the final electrode configuration in delivery of neurostimulation therapy.

9. The method of claim 8, wherein the neurostimulator is a spinal cord stimulator, and the final electrode configuration includes electrodes deployed on one more implanted spinal leads.

10. The method of claim 9, wherein the set of electrodes comprises at least eight electrodes.

11. The method of claim 1, wherein selecting the first and second electrode configurations includes suggesting the first and second electrode configurations to a clinician.

12. The method of claim 1, wherein receiving an indication relating to observed efficacy includes receiving user input indicating observed efficacy.

13. The method of claim 1, further comprising updating the genetic algorithm based on the observed efficacy.

14. The method of claim 13, wherein updating the genetic algorithm comprises performing at least one of cross-over between different solutions identified by the genetic algorithm or mutation of one or more solutions identified by the genetic algorithm.

15. The method of claim 14, wherein the genetic algorithm identifies solutions associated with the first and second electrode configurations, and updating the genetic algorithm includes generating one or more successive generations of the solutions.

16. The method of claim 14, Wherein cross-over includes swapping electrodes between different solutions.

17. The method of claim 14, wherein mutation includes introducing random electrode changes in different solutions.

18. A computer-readable medium comprising instructions to cause a processor to:
select a first electrode configuration for a neurostimulator;
receive an indication of observed efficacy of the first electrode configuration; and
select a second electrode configuration for the neurostimulator based on the indication of observed efficacy and a genetic algorithm, wherein each of the electrode configurations defines a combination of particular electrodes selected from a set of electrodes for delivery of neurostimulation energy, the electrode configurations further defining polarities for each of the electrodes in the combination.

19. The computer-readable medium of claim 18, wherein the electrodes are carried by two or more implanted leads.

20. The computer-readable medium of claim 19, wherein the electrodes are associated with different target regions within a body of a patient.

21. The computer-readable medium of claim 19, wherein the leads are implanted proximate a spine of a patient.

22. The computer-readable medium of claim 18, further comprising instructions to cause the processor to iteratively select additional electrode configurations for the neurostimulator based on observed efficacy of preceding electrode configurations and the genetic algorithm.

23. The computer-readable medium of claim 22, further comprising instructions to cause the processor to terminate the iterative selection of the additional electrode configurations when one or more termination criteria are satisfied.

24. The computer-readable medium of claim 23, wherein the termination criteria include selection of one of the electrode configurations with an observed efficacy that satisfies a threshold efficacy.

25. The computer-readable medium of claim 18, further comprising instructions to cause the processor to:
iteratively select additional electrode configurations for the neurostimulator based on observed efficacy of preceding electrode configurations and the genetic algorithm;
terminate the iterative selection of the additional electrode configurations at a final electrode configuration when one or more termination criteria are satisfied; and
program the neurostimulator to employ the final electrode configuration in delivery of neurostimulation therapy.

26. The computer-readable medium of claim 25, wherein the neurostimulator is a spinal cord stimulator, and the final electrode configuration includes electrodes deployed on one more implanted spinal leads.

27. The computer-readable medium of claim 26, wherein the set of electrodes comprises at least eight electrodes.

28. The computer-readable medium of claim 18, wherein the instructions cause the processor to suggest the first and second electrode configurations to a clinician.

29. The computer-readable medium of claim 18, wherein the instructions to cause the processor to receive an indication relating to observed efficacy include instructions to cause the processor to receive user input indicating observed efficacy.

30. The computer-readable medium of claim 18, further comprising updating the genetic algorithm based on the observed efficacy.

31. The computer-readable medium of claim 30, wherein updating the genetic algorithm comprises performing at least one of cross-over between different solutions identified by the genetic algorithm or mutation of one or more solutions identified by the genetic algorithm.

32. The computer-readable medium of claim 31, wherein the genetic algorithm identifies solutions associated with the first and second electrode configurations, and updating the genetic algorithm includes generating one or more successive generations of the solutions.

33. The computer-readable medium of claim 31, wherein cross-over includes swapping electrodes between different solutions.

34. The computer-readable medium of claim 31, wherein mutation includes introducing random electrode changes in different solutions.

35. A device comprising a processor programmed to:
select a first electrode configuration for a neurostimulator;
receive an indication of observed efficacy of the first electrode configuration; and
select a second electrode configuration for the neurostimulator based on the indication of observed efficacy and a genetic algorithm, wherein each of the electrode configurations defines a combination of particular electrodes selected from a set of electrodes for delivery of neurostimulation energy, the electrode configurations further defining polarities for each of the electrodes in the combination.

36. The device of claim 35, wherein the electrodes are carried by two or more implanted leads.

37. The device of claim 36, wherein the electrodes are associated with different target regions within a body of a patient.

38. The device of claim 36, wherein the leads are implanted proximate a spine of a patient.

39. The device of claim 35, wherein the processor iteratively selects additional electrode configurations for the neurostimulator based on observed efficacy of preceding electrode configurations and the genetic algorithm.

40. The device of claim 39, wherein the processor terminates the iterative selection of the additional electrode configurations when one or more termination criteria are satisfied.

41. The device of claim 40, wherein the termination criteria include selection of one of the electrode configurations with an observed efficacy that satisfies a threshold efficacy.

42. The device of claim 35, wherein the processor:
iteratively selects additional electrode configurations for the neurostimulator based on observed efficacy of preceding electrode configurations and the genetic algorithm;
terminates the iterative selection of the additional electrode configurations at a final electrode configuration when one or more termination criteria are satisfied; and
programs the neurostimulator to employ the final electrode configuration in delivery of neurostimulation therapy.

43. The device of claim 42, wherein the neurostimulator is a spinal cord stimulator, and the final electrode configuration includes electrodes deployed on one more implanted spinal leads.

44. The device of claim 43, wherein the set of electrodes comprises at least eight electrodes.

45. The device of claim 35, wherein the processor generates a suggestion of the first and second electrode configurations to a clinician.

46. The device of claim 35, wherein the processor receives user input indicating observed efficacy.

47. The device of claim 35, wherein the processor updates the genetic algorithm based on the observed efficacy.

48. The device of claim 47, wherein the processor updates the genetic algorithm by performing at least one of cross-over between different solutions identified by the genetic algorithm or mutation of one or more solutions identified by the genetic algorithm.

49. The device of claim 48, wherein the genetic algorithm identifies solutions associated with the first and second electrode configurations, and the processor updates the genetic algorithm by generating one or more successive generations of the solutions.

50. The device of claim 48, wherein cross-over includes swapping electrodes between different solutions.

51. The device of claim 48, wherein mutation includes introducing random electrode changes in different solutions.

* * * * *